(12) United States Patent
Wang et al.

(10) Patent No.: US 7,636,157 B2
(45) Date of Patent: Dec. 22, 2009

(54) METHOD AND APPARATUS FOR CONDUCTING RAMAN SPECTROSCOPY

(75) Inventors: Peidong Wang, Carlisle, MA (US); Daryoosh Vakhshoori, Cambridge, MA (US); Yu Shen, Waltham, MA (US); Kevin J. Knopp, Newburyport, MA (US); Masud Azimi, Belmont, MA (US)

(73) Assignee: Ahura Corporation, Wilmington, MA (US)

( * ) Notice: Subject to any disclaimer, the term of this patent is extended or adjusted under 35 U.S.C. 154(b) by 433 days.

(21) Appl. No.: 11/117,940

(22) Filed: Apr. 29, 2005

(65) Prior Publication Data

US 2005/0248759 A1 Nov. 10, 2005

Related U.S. Application Data

(60) Provisional application No. 60/566,713, filed on Apr. 30, 2004, provisional application No. 60/607,735, filed on Sep. 7, 2004.

(51) Int. Cl.
*G01J 3/44* (2006.01)
(52) U.S. Cl. ..................................... 356/301
(58) Field of Classification Search .................. 356/301
See application file for complete search history.

(56) References Cited

U.S. PATENT DOCUMENTS

| | | | |
|---|---|---|---|
| 3,017,513 A | 1/1962 | Messelt | |
| 3,906,241 A | 9/1975 | Thompson | |
| 4,930,872 A | 6/1990 | Convery | |
| 5,026,160 A | 6/1991 | Dorain et al. | |
| 5,048,959 A | 9/1991 | Morris et al. | |
| 5,260,639 A | 11/1993 | De Young et al. | |
| 5,377,004 A * | 12/1994 | Owen et al. | 356/301 |
| 5,483,337 A | 1/1996 | Barnard et al. | |
| 5,550,375 A | 8/1996 | Peters et al. | |
| 5,615,673 A | 4/1997 | Berger et al. | |

(Continued)

FOREIGN PATENT DOCUMENTS

WO    2006/080939    8/2006

(Continued)

OTHER PUBLICATIONS

Eckenrode, Brian A. et al., Portable Raman Spectroscopy Systems for Field Analysis, Forensic Science Communications, Oct. 2001, vol. 3, No. 4.

(Continued)

*Primary Examiner*—Kara E Geisel
(74) *Attorney, Agent, or Firm*—Fish & Richardson P.C.

(57) ABSTRACT

Disclosed herein are Raman probes that include: (a) a first optical fiber for receiving laser excitation light from a light source and transmitting the same; (b) a first filter for receiving light from the first optical fiber and adapted to pass the laser excitation light and to block spurious signals associated with the light; (c) a second filter for receiving light from the first filter and adapted to direct the light toward a specimen; and (d) focusing apparatus for receiving the light from the second filter, focusing the light on the specimen so as to generate the Raman signal, and returning the Raman signal to the second filter. The second filter is further configured so that when the second filter receives the Raman signal from the focusing apparatus, the second filter filters out unwanted laser excitation light before directing the Raman signal to a second optical fiber.

45 Claims, 14 Drawing Sheets

U.S. PATENT DOCUMENTS

| | | | |
|---|---|---|---|
| 5,651,018 | A | 7/1997 | Mehuys et al. |
| 5,659,566 | A | 8/1997 | Takemoto |
| 5,734,165 | A | 3/1998 | Unal et al. |
| 5,828,450 | A | 10/1998 | Dou et al. |
| 5,850,623 | A | 12/1998 | Carman, Jr. et al. |
| 6,002,476 | A * | 12/1999 | Treado .................. 356/301 |
| 6,018,535 | A | 1/2000 | Maeda |
| 6,038,363 | A * | 3/2000 | Slater et al. ............ 356/301 |
| 6,045,502 | A | 4/2000 | Eppstein et al. |
| 6,069,689 | A | 5/2000 | Zeng et al. |
| 6,082,724 | A | 7/2000 | Kahlig et al. |
| 6,249,349 | B1 | 6/2001 | Lauer |
| 6,303,934 | B1 | 10/2001 | Daly et al. |
| 6,373,567 | B1 | 4/2002 | Wise et al. |
| 6,510,257 | B1 | 1/2003 | Barwicz et al. |
| 6,526,071 | B1 | 2/2003 | Zorabedian et al. |
| 6,608,677 | B1 | 8/2003 | Ray et al. |
| 6,612,559 | B2 | 9/2003 | Boss |
| 6,625,182 | B1 | 9/2003 | Kuksenkov et al. |
| 6,636,304 | B2 * | 10/2003 | Gilby .................... 356/318 |
| 6,636,536 | B1 | 10/2003 | Tisue |
| 6,707,548 | B2 * | 3/2004 | Kreimer et al. ......... 356/301 |
| 6,771,369 | B2 | 8/2004 | Rzasa et al. |
| 6,803,328 | B2 | 10/2004 | McCullough |
| 6,862,092 | B1 | 3/2005 | Ibsen et al. |
| 6,879,621 | B2 | 4/2005 | Heck et al. |
| 6,907,149 | B2 * | 6/2005 | Slater .................... 356/301 |
| 6,919,959 | B2 | 7/2005 | Masten |
| 6,959,248 | B2 | 10/2005 | Gard et al. |
| 6,977,723 | B2 | 12/2005 | Lemmo et al. |
| 6,992,759 | B2 | 1/2006 | Nakayama et al. |
| 7,092,090 | B2 | 8/2006 | Shimizu et al. |
| 7,099,004 | B2 | 8/2006 | Masten |
| 7,110,109 | B2 | 9/2006 | Knopp et al. |
| 7,148,963 | B2 * | 12/2006 | Owen et al. ............ 356/301 |
| 7,289,208 | B2 | 10/2007 | Vakhshoori et al. |
| 2002/0015433 | A1 | 2/2002 | Zimmermann |
| 2002/0033944 | A1 | 3/2002 | Sharts et al. |
| 2002/0085598 | A1 | 7/2002 | Shaw |
| 2002/0101019 | A1 | 8/2002 | Boss |
| 2002/0154301 | A1 | 10/2002 | Shen et al. |
| 2003/0002548 | A1 | 1/2003 | Boscha |
| 2003/0002839 | A1 | 1/2003 | Clow et al. |
| 2003/0030800 | A1 * | 2/2003 | Golden et al. ......... 356/301 |
| 2003/0085348 | A1 | 5/2003 | Megerle |
| 2003/0142302 | A1 | 7/2003 | Jiang |
| 2003/0147593 | A1 | 8/2003 | Slater |
| 2003/0179472 | A1 | 9/2003 | Schaefer et al. |
| 2003/0197860 | A1 | 10/2003 | Rice |
| 2003/0219046 | A1 | 11/2003 | Kitaoka et al. |
| 2003/0227628 | A1 * | 12/2003 | Kreimer et al. ......... 356/419 |
| 2004/0039274 | A1 | 2/2004 | Benaron et al. |
| 2004/0058386 | A1 | 3/2004 | Wishart et al. |
| 2004/0109230 | A1 | 6/2004 | Matsushita et al. |
| 2004/0130714 | A1 | 7/2004 | Gellerman et al. |
| 2004/0165183 | A1 | 8/2004 | Marquardt et al. |
| 2004/0165254 | A1 | 8/2004 | Tokura et al. |
| 2004/0190679 | A1 | 9/2004 | Waggener et al. |
| 2004/0217383 | A1 | 11/2004 | Krames et al. |
| 2004/0252299 | A9 | 12/2004 | Lemmo et al. |
| 2004/0263843 | A1 | 12/2004 | Knopp et al. |
| 2005/0006590 | A1 | 1/2005 | Harrison |
| 2005/0018721 | A1 | 1/2005 | Kish et al. |
| 2005/0083521 | A1 | 4/2005 | Kamerman |
| 2006/0023209 | A1 | 2/2006 | Lee et al. |
| 2006/0045147 | A1 | 3/2006 | Sin et al. |
| 2006/0045151 | A1 | 3/2006 | Vakhshoori et al. |
| 2006/0088069 | A1 | 4/2006 | Vakhshoori et al. |
| 2006/0170917 | A1 | 8/2006 | Vakhshoori et al. |
| 2006/0203862 | A1 | 9/2006 | Bonen et al. |
| 2007/0002319 | A1 | 1/2007 | Knopp et al. |
| 2007/0024848 | A1 | 2/2007 | Knopp et al. |
| 2007/0116069 | A1 | 5/2007 | Wang et al. |
| 2008/0002746 | A1 | 1/2008 | Narayan |
| 2008/0033663 | A1 | 2/2008 | Brown et al. |
| 2008/0170223 | A1 | 7/2008 | Vakhshoori et al. |
| 2009/0033928 | A1 | 2/2009 | Azimi et al. |

OTHER PUBLICATIONS

Harvey, S.D. et al., Blind field test evaluation of Raman spectroscopy as a forensic tool, Forensic Science International, Dec. 21, 2002, 125.
Moore, D.S., Instrumentation for trace detection of high explosives, Aug. 2004, 2499-2512, vol. 75, No. 8.
Cleij et al., "Reproducibility as the Basis of a Similarity Index for Continuous Variables in Straightforward Library Search Methods," Analytica Chimica Acta, vol. 150:29-36 (1983).
http://en.wikipedia.org/wiki/Coefficient_of_thermal_expansion, downloaded on Oct. 16, 2008.
Li et al., "Comparison of Spectra Using a Bayesian Approach. An Argument using Oil Spills as an Example," Analytical Chemistry, vol. 77:639-644 (2005).
Lowry, "Automated Spectral Searching in Infrared, Raman and Near-Infrared Spectroscopy," J. Wiley & Sons Ltd., pp. 1948-1961 (2002).
*McGraw-Hill Dictionary of Scientific and Technical Terms*, Sixth Edition, McGraw Hill, New York, 2003, p. 421.
*Physics For Scientists and Engineers with Modern Physics*: Fourth Edition, Raymond A. Serway, Saunders, Saunders College Publishing, Philadelphia, 1996, pp. 536-539.

* cited by examiner

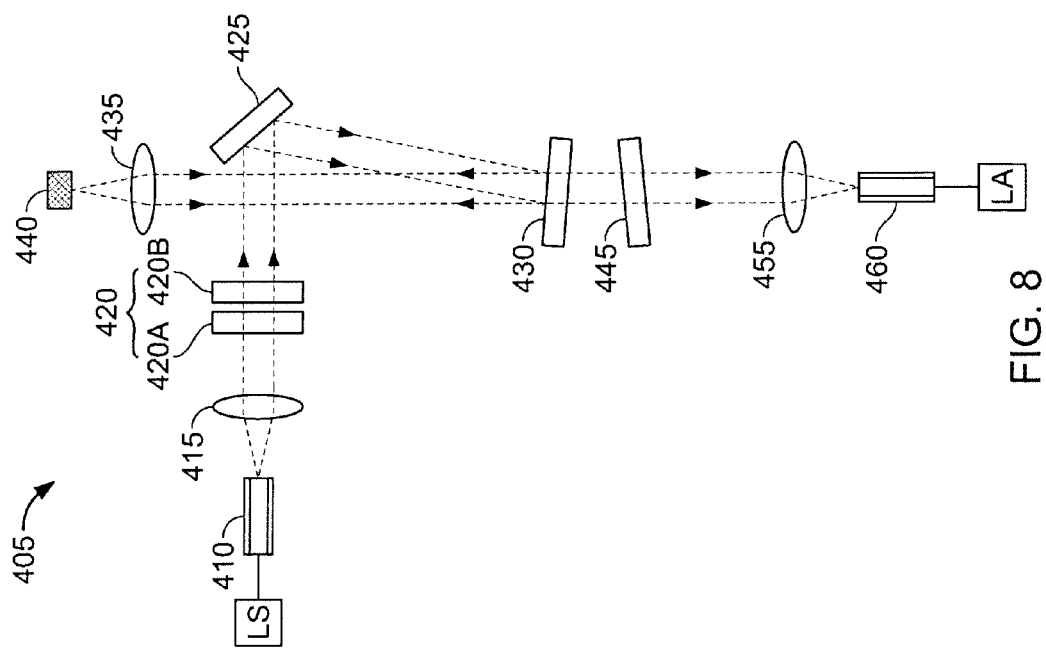
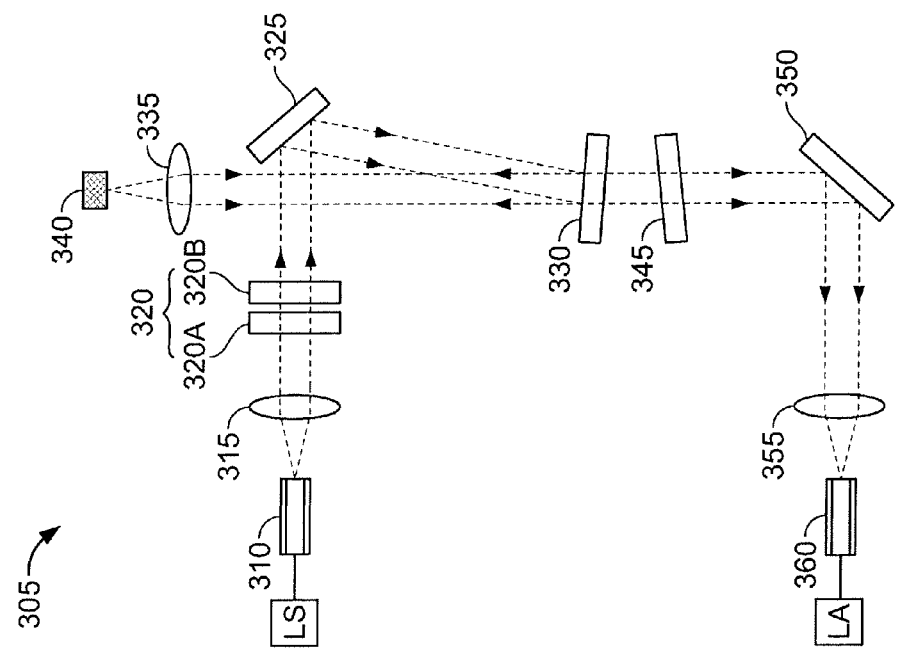
FIG. 8
FIG. 7

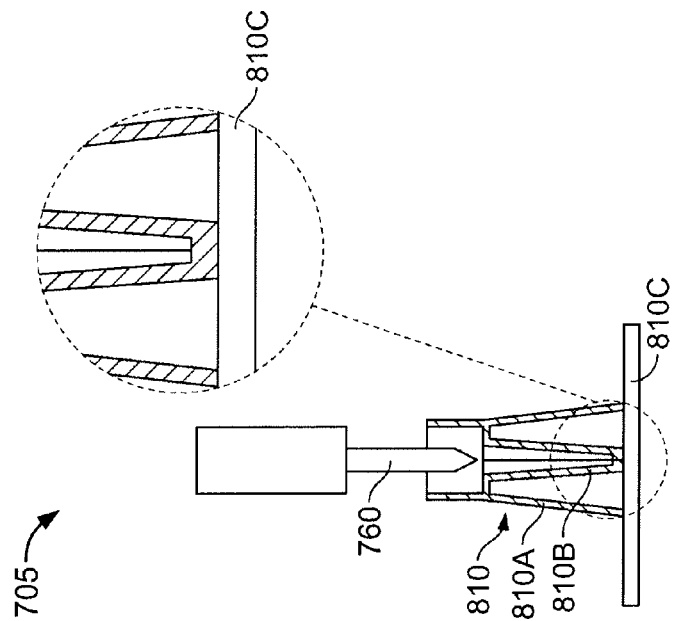
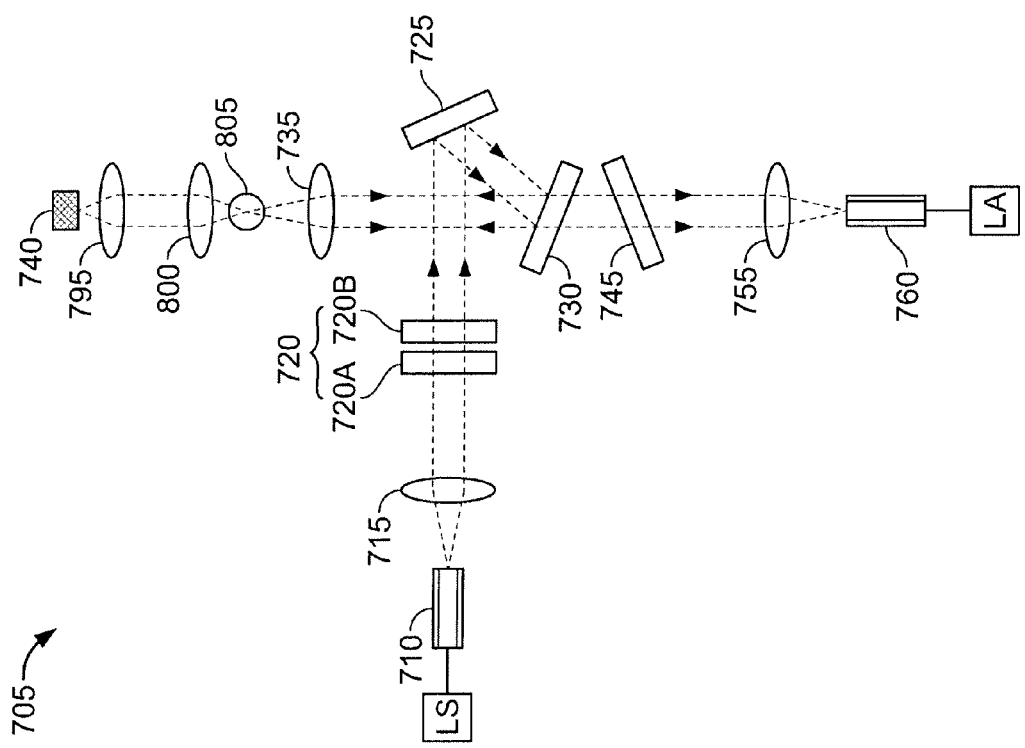

METHOD AND APPARATUS FOR CONDUCTING RAMAN SPECTROSCOPY

REFERENCE TO PENDING PRIOR PATENT APPLICATIONS

This patent application claims benefit of:
(i) pending prior U.S. Provisional Patent Application Ser. No. 60/566,713, filed Apr. 30, 2004 by Peidong Wang et al. for RAMAN SPECTROSCOPY TECHNIQUES OVER OPTICAL FIBERS; and
(ii) pending prior U.S. Provisional Patent Application Ser. No. 60/607,735, filed Sep. 7, 2004 by Kevin Knopp et al. for RAMAN PROBE WITH INLINE VIAL CAPABILITY.

The two above-identified patent applications are hereby incorporated herein by reference.

FIELD OF THE INVENTION

This invention relates to methods and apparatus for identifying and characterizing substances in general, and more particularly to methods and apparatus for identifying and characterizing substances using Raman spectroscopy.

BACKGROUND OF THE INVENTION

Raman spectroscopy is a viable technique for identifying and characterizing a vast array of substances. Raman spectroscopy is widely used in both the scientific and commercial areas. By way of example but not limitation, commercial areas of use currently include medicine, biotechnology, pharmaceuticals, security and geology. In addition, recent technological advances are making it possible to increase the range of applications using Raman spectroscopy through a reduction in cost and size. For example, portable units have recently become available for out-of-lab uses such as the measurement and identification of powders, pills, liquids, etc.

Unfortunately, a number of problems exist with respect to current Raman spectroscopy systems. For example, a persistent problem in existing Raman spectroscopy systems is the delivery of laser light to the specimen and the collection of the Raman signature from the specimen. Among other things, these problems include space limitations in portable Raman systems, signal distortions introduced into the system due to Amplified Spontaneous Emission (ASE) from the laser sources, etc.

Also, for Raman spectroscopy of specimens which are located remotely from the light sources and light detectors, optical fibers are commonly used to deliver the excitation light and to collect the Raman signals. However, the use of these optical fibers can introduce fluorescence and Raleigh and Raman scatterings generated through interactions in the optical fibers.

Accordingly, a primary object of the present invention is to provide an improved Raman spectroscopy system which overcomes the shortcomings of currently available systems.

SUMMARY OF THE INVENTION

In one preferred embodiment of the present invention, there is provided an improved Raman spectroscopy system (sometimes hereinafter referred to as a Raman probe) in which a set of optical elements is used to separate the pump source from the Raman signal and to direct the Raman signal to a remote spectrometer or detector. The Raman probe is preferably also configured so as to be able to filter ASE background from the laser sources, as well as to filter fluorescence and Raleigh and Raman scatterings generated through interactions in the optical fibers.

In another form of the present invention, there is provided a Raman probe comprising:
a first optical fiber for receiving laser excitation light from a light source and transmitting the same;
a first filter for receiving light from the first optical fiber and adapted to pass the laser excitation light and to block spurious signals associated with the light;
a second filter for receiving light from the first filter and adapted to direct the light toward a specimen;
focusing apparatus for receiving the light from the second filter, focusing the light on the specimen so as to generate the Raman signal, and returning the Raman signal to the second filter;
wherein the second filter is further configured so that when the second filter receives the Raman signal from the focusing apparatus, the second filter filters out unwanted laser excitation light before directing the Raman signal to a second optical fiber; and
a second optical fiber for receiving the Raman signal from the second filter and transmitting the same to a light analyzer.

And in one preferred embodiment of the invention, a novel optical probe delivery system is provided which offers three unique modes of use for exciting and collecting light from the specimen under test, all encompassed with one optical probe design. In a first mode of use, the Raman probe allows the user to maintain distance from the specimen by using a conical standoff, which provides both distance control and laser safety by limiting the exposed beams. The second mode of use allows the user to remove the conical standoff so as to maintain distance control by hand or other means. The third mode of use allows a specimen vial to be inserted directly within the probe optics assembly.

In another form of the present invention, there is provided a Raman probe comprising:
a light source for generating laser excitation light;
focusing apparatus for receiving the laser excitation light from the light source, focusing the laser excitation light on a specimen so as to generate the Raman signal, and returning the Raman signal to a light analyzer; and
a light analyzer for analyzing the Raman signature of the specimen, whereby to identify the specimen;
wherein the focusing apparatus is configured to permit the specimen to reside in a vial receptacle or at a target location remote from the vial receptacle.

In another form of the present invention, there is provided a method for conducting Raman spectroscopy of a specimen, comprising:
generating laser excitation light using a light source;
passing the laser excitation light through a first filter so as to block spurious signals associated with the light;
directing the laser excitation light to a second filter so as to direct the laser excitation light toward the specimen;
receiving the light from the second filter, focusing the light on the specimen so as to generate the Raman signal, and returning the Raman signal to the second filter;
wherein the second filter is further configured so that when the second filter receives the Raman signal from the specimen, the second filter filters out unwanted laser excitation light;
passing the filtered light received from the second filter to a light analyzer; and
analyzing the Raman signature of the specimen so as to identify the specimen.

In another form of the present invention, there is provided a Raman probe comprising:

a housing;

a light source disposed within the housing for generating laser excitation light;

focusing apparatus disposed within the housing for receiving the laser excitation light from the light source, focusing the laser excitation light on a specimen so as to generate the Raman signal, and returning the Raman signal to a light analyzer; and a light analyzer disposed within the housing for analyzing the Raman signature of the specimen, whereby to identify the specimen;

wherein the focusing apparatus is configured to permit the specimen to reside at a target location remote from the housing;

and further comprising an optical shield mounted to the housing so as to be disposed between the specimen and the user, whereby to optically shield the user from the light source.

In another form of the present invention, there is provided a Raman probe comprising:

a housing;

a light source disposed within the housing for generating laser excitation light;

focusing apparatus disposed within the housing for receiving the laser excitation light from the light source, focusing the laser excitation light on a specimen so as to generate the Raman signal, and returning the Raman signal to a light analyzer; and a light analyzer disposed within the housing for analyzing the Raman signature of the specimen, whereby to identify the specimen;

wherein the focusing apparatus is configured to permit the specimen to reside at a target location remote from the housing;

and further comprising a camera mounted to the housing so that its field of view encompasses the target location, and a display mounted to the housing for displaying the image captured by the camera, whereby to permit the user to position the probe relative to the specimen while watching the display.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIG. 7 illustrates another embodiment which is similar to that of FIG. 1, except using a 5 degree of Angle Of Incidence (AOI) for the filters;

FIG. 8 illustrates another embodiment which is similar to that of FIG. 5, except using a 5 degree of Angle Of Incidence (AOI) for the filters;

FIG. 11 illustrates a portable Raman probe which is configured to allow three different methods of use;

FIGS. 12 and 13 illustrate the portable Raman probe of FIG. 11 configured to allow the user to maintain distance from the specimen using a conical standoff;

DETAILED DESCRIPTION OF THE PREFERRED EMBODIMENTS

Novel Raman Spectroscope

Figure 1A:
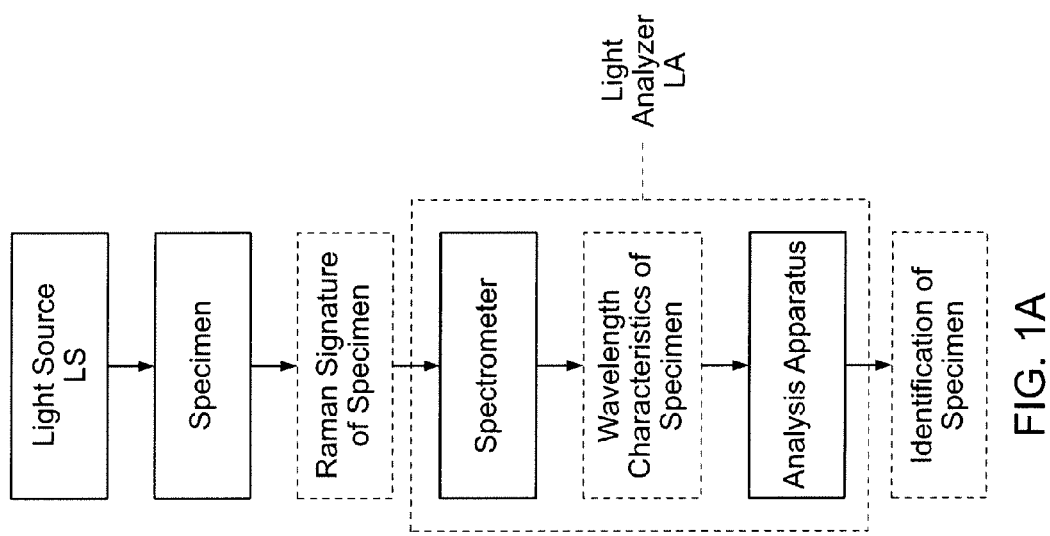
FIG. 1A illustrates the overall Raman spectroscopy system in schematic form.
Figure 1:
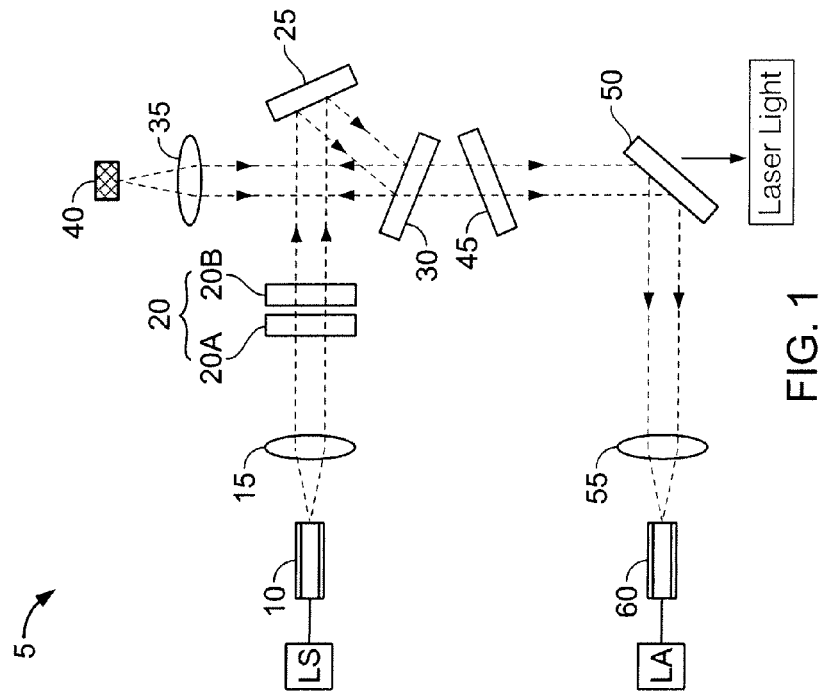
FIG. 1 illustrates a novel Raman optical probe.

Looking first at FIG. 1, there is shown a novel Raman probe 5. The excitation light source LS in this arrangement may be, for example, one or more 785 nm semiconductor lasers with limited linewidths. However, the Raman probe 5 may also use any other laser source as the excitation light source LS as long as the laser source is compatible with Raman spectroscopy detection techniques. The output of excitation light source LS is delivered through optical fiber 10 and collimated through lens 15. A bandpass filter 20 (or multiple combination of bandpass filters 20A, 20B) is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 10. Preferably bandpass filter 20 is adapted to block spurious signals associated with both the laser and the fiber. The laser excitation light is then reflected by filters 25 (at a 22.5 degree Angle of Optical Incidence, AOI) and 30 (at a 22.5 degree AOI), and then it is focused through lens 35 to excite specimen 40. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. In one preferred embodiment of the present invention, filters 25 and 30 are preferably long-pass filters. In this respect it should also be appreciated that filter 25 may be replaced by a simple reflector to reflect the laser light. After the laser excitation light has been projected on the specimen, the Raman signal is re-collimated through lens 35 and passed through filter 30. Alternatively, the Raman signal may pass through multiple filters (i.e., in addition to passing through filter 30, the Raman signal may pass through additional filter 45, at a 22.5 degree AOI). In one preferred embodiment of the present invention, additional filter 45 is preferably also a long-pass filter. When the Raman signal from the specimen is passed though filter 30, filter 30 serves a second purpose at this time, i.e., it blocks the laser line. Filters 30 and 45 can provide up to >OD10 filtration of the laser line before the light is redirected through broadband reflector 50 (at a 45 degree AOI) and focus lens 55 into collecting optical fibers 60. Optical fibers 60 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form. In addition to reflecting the Raman signal, broadband reflector 50 also filters out laser excitation light (OD1).

Dielectric Thin Film Filters

The various filtering described above may be accomplished by the following dielectric thin film filters. In this respect, for the purposes of the present disclosure, it will be assumed that the Raman signal of interest is >300 cm−1. Raman signal that is close to the excitation source (i.e., about 100 cm−1 to about 300 cm−1) can also be detected through another set of filters.

(1) Passband Filter Design.

Figure 2:
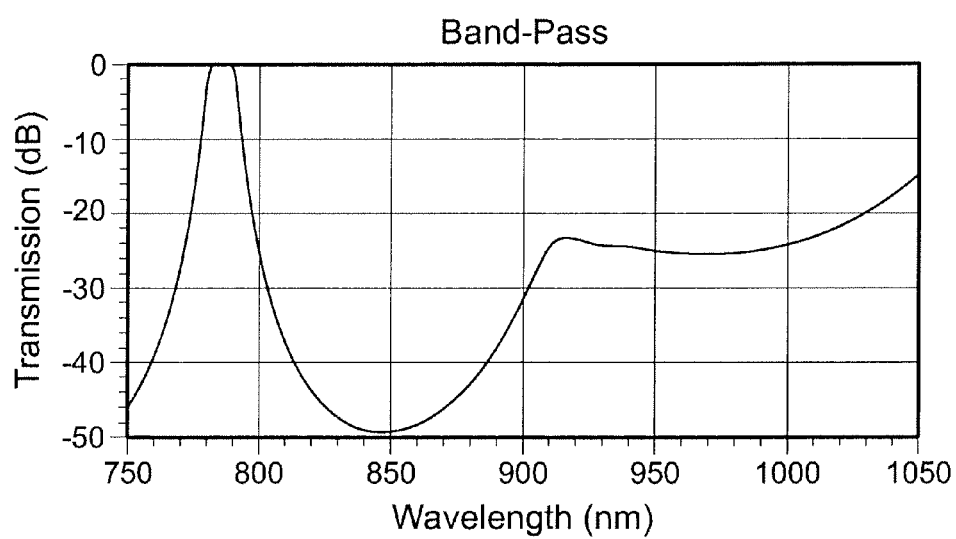
FIG. 2 illustrates a thin film design to filter out the ASE, fluorescence and Raleigh and Raman scattering from the fibers.

As noted above, one or more passband filters 20A, 20B can be used to pass the laser light and block spurious signals associated with the laser, the fiber, and/or both. A passband filter can be constructed using a dielectric thin film construction. See, for example, FIG. 2, which illustrates the transmission characteristics of a thin film design configured to filter out laser ASE, and the fluorescence and Raleigh and Raman scattering in the fibers.

(2) Filter Design.

Figure 3:
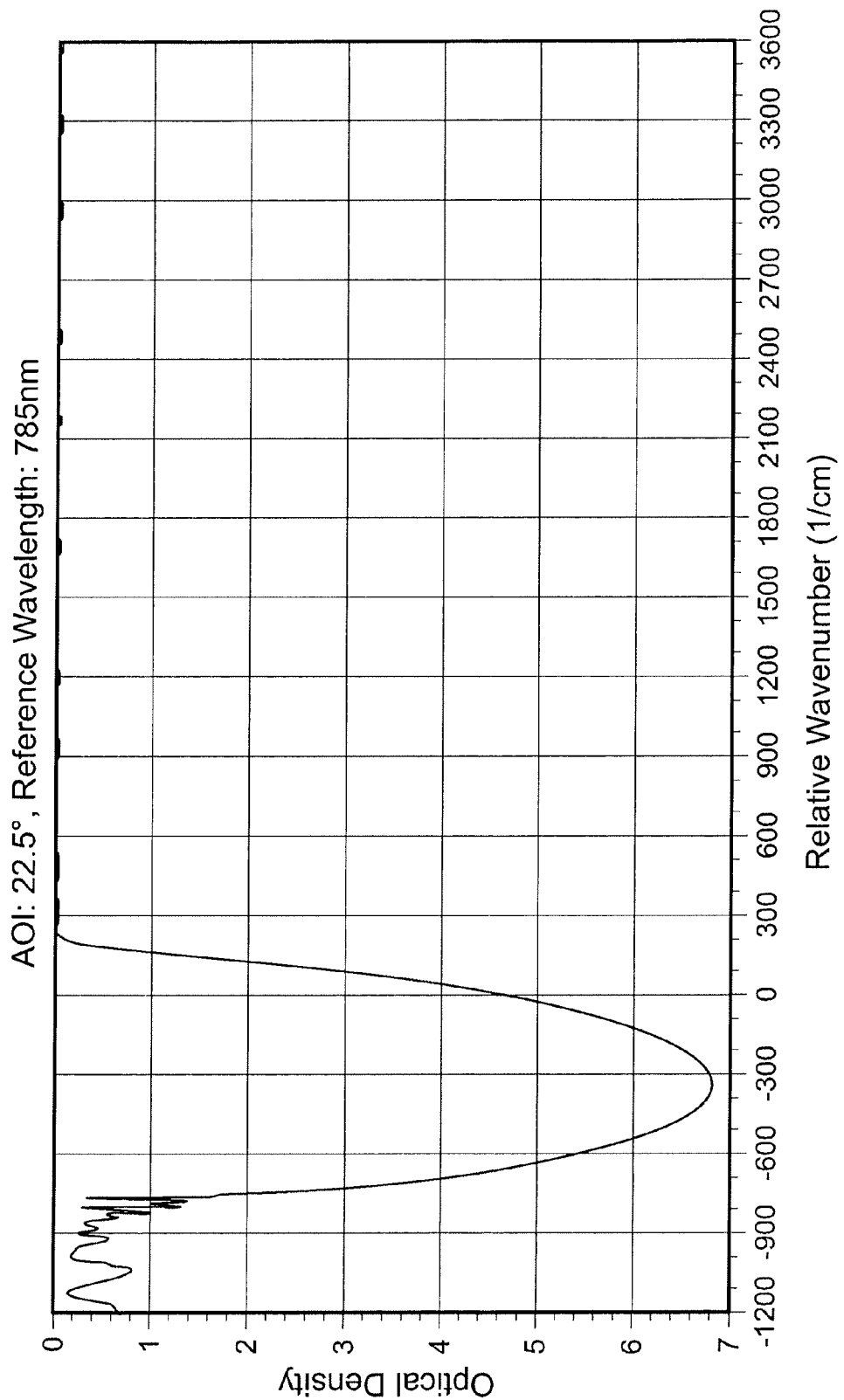
FIG. 3 illustrates thin films designed for reflective (blocking) laser lines and transmitting Raman signals.

As also noted above, filters 25, 30 and/or 45 (in one embodiment of the invention, preferably long-pass filters) can be used to reflect or block the laser line and to pass the Raman signals. Such filters can be constructed using dielectric thin film constructions. The design is preferably configured for the range of 800 nm-1100 nm; the CCD detector is generally not sensitive beyond this range. See, for example, FIG. 3, which illustrates the transmission characteristics of a filter thin film design for reflecting (and/or blocking) laser lines and for transmitting Raman signals.

(3) Additional Broadband Reflector.

Figure 4:
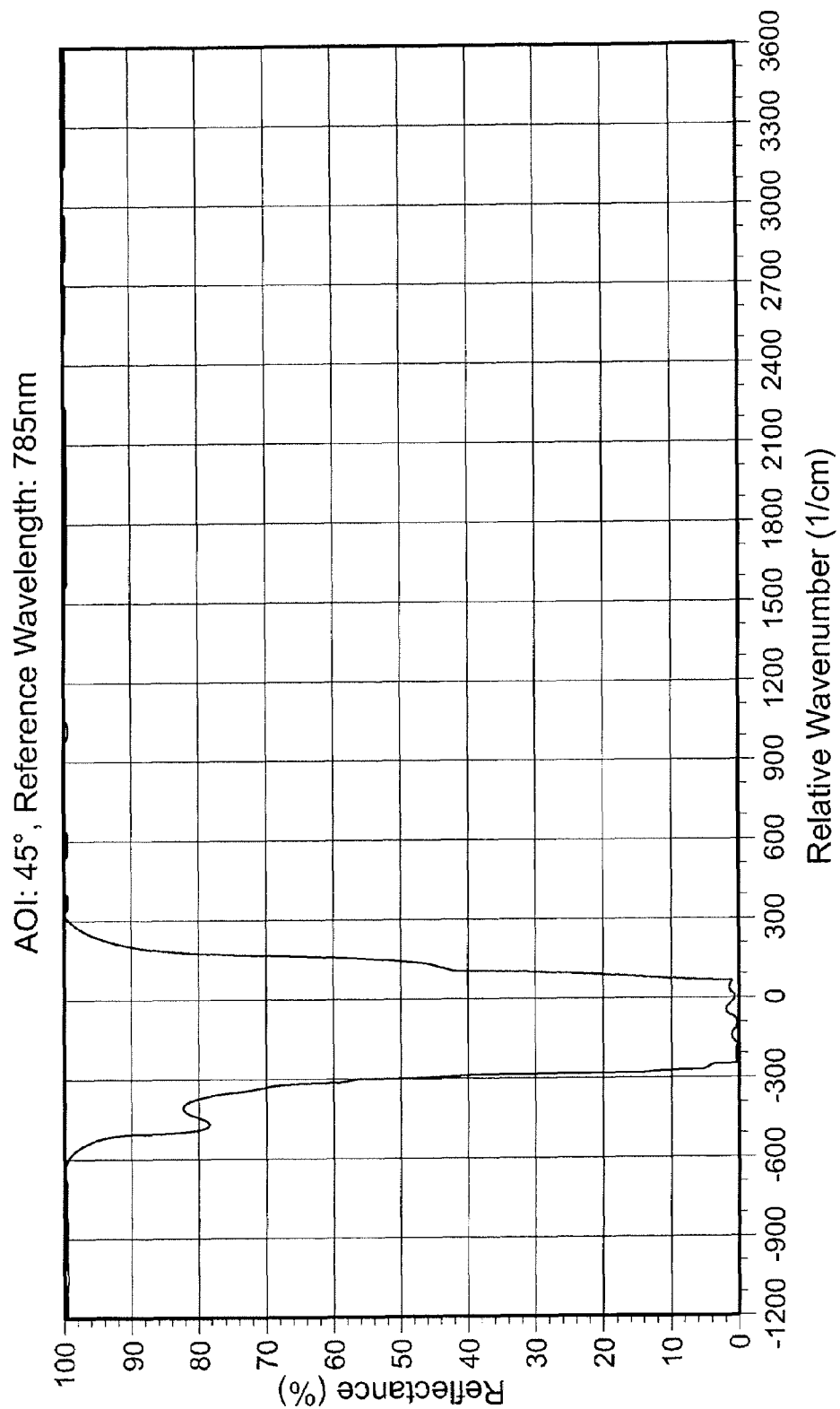
FIG. 4 illustrates an additional broadband reflector to direct Raman signals and blocking the laser lines.

The additional broadband reflector 50 is used to redirect the Raman signal to the collecting fibers. In addition, the additional broadband reflector 50 further filters the laser excitation light (OD>1) before passing the light to the collecting fibers. The broadband reflector 50 can also be constructed using dielectric thin film constructions. See, for example, FIG. 4, which illustrates the transmission characteristics of an additional broadband reflector 50 configured to direct Raman signals and block the laser lines.

Additional Novel Constructions

Figure 5:
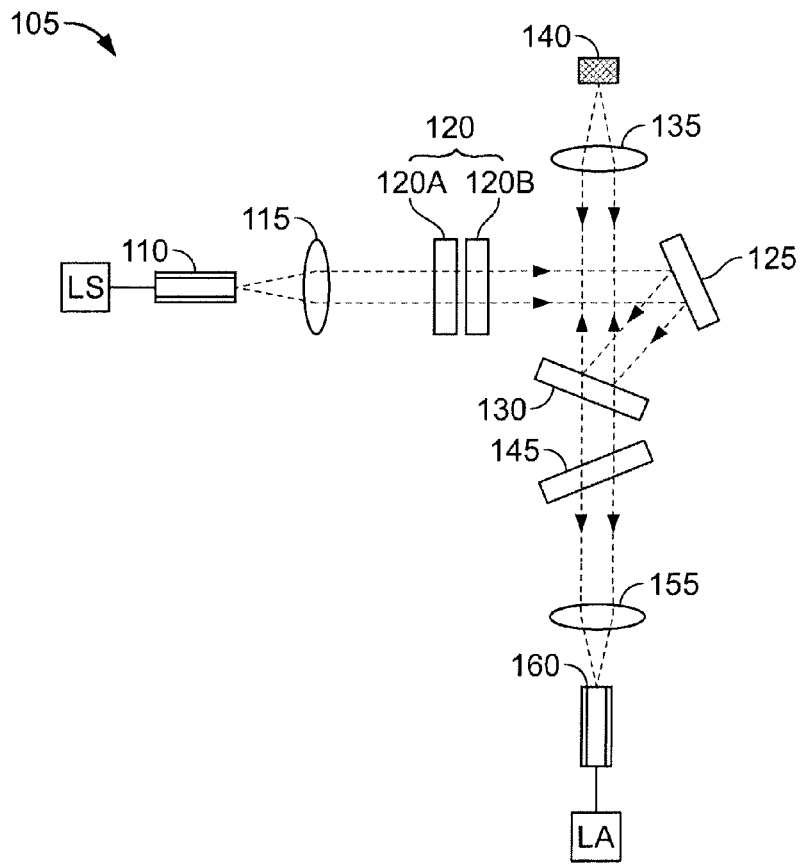
FIG. 5 illustrates another Raman probe layout where the broadband reflector is omitted through the rearrangement of collecting fibers.

Looking now at FIG. 5, there is shown another novel Raman probe layout 105 which is generally similar in construction to that shown in FIG. 1, except that the broadband reflector 50 is omitted through the rearrangement of the collecting fibers. Thus, in the construction shown in FIG. 5, the output of excitation light source LS is delivered through optical fiber 110 and collimated through lens 115. A bandpass filter 120 (or multiple combination of bandpass filters 120A, 120B) is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 110. Preferably bandpass filter 120 is adapted to block spurious signals associated with both the laser and the fiber. The laser excitation light is then reflected by filters 125 (at a 22.5 degree AOI) and 130 (at a 22.5 degree AOI), and then it is focused through lens 135 to excite specimen 140. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. In one preferred embodiment of the present invention, filters 125 and 130 are preferably long-pass filters. In this respect it should also be appreciated that filter 125 may be replaced by a simple reflector to reflect the laser light. After the laser excitation light has been projected on the specimen, the Raman signal is re-collimated through lens 135 and passed through filter 130. Alternatively, the Raman signal may pass through multiple filters (i.e., in addition to passing through filter 130, the Raman signal may pass through additional filter 145, at a 22.5 degree AOI). In one preferred embodiment of the present invention, additional filter 145 is preferably also a long-pass filter. When the Raman signal from the specimen is passed though filter 130, filter 130 serves a second purpose at this time, i.e., it blocks the laser line. Filters 130 and 145 can provide up to >OD10 filtration of the laser line before the light is redirected by focus lens 155 into collecting optical fibers 160. Optical fibers 160 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form.

Figure 6:
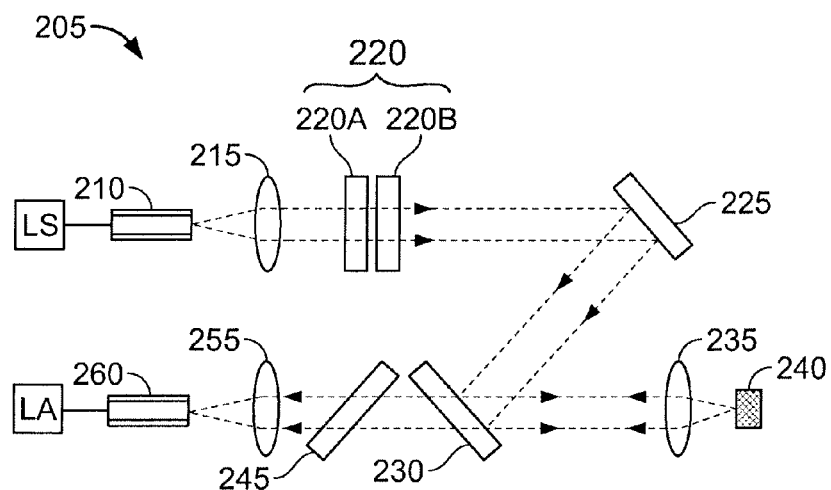
FIG. 6 illustrates another embodiment of the present invention, wherein the fibers and signal collecting optics are collinear (as opposed to being perpendicular to each other)

Looking next at FIG. 6, there is shown another novel Raman probe layout 205 which is generally similar to the construction shown in FIG. 5; however, with this novel arrangement, the fibers and signal collecting optics are collinear with one another (rather than being perpendicular to one another). Thus, in the construction shown in FIG. 6, the output of excitation light source LS is delivered through optical fiber 210 and collimated through lens 215. A bandpass filter 220 (or multiple combination of bandpass filters 220A, 220B) is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 210. Preferably bandpass filter 220 is adapted to block spurious signals associated with both the laser and the fiber. The laser excitation light is then reflected by filters 225 (at a 22.5 degree AOI) and 230 (at a 22.5 degree AOI), and then it is focused through lens 235 to excite specimen 240. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. In one preferred embodiment of the present invention, filters 225 and 230 are preferably long-pass filters. In this respect it should also be appreciated that filter 225 may be replaced by a simple reflector to reflect the laser light. After the laser excitation light has been projected on the specimen, the Raman signal is re-collimated through lens 235 and passed through filter 230. Alternatively, the Raman signal may pass through multiple filters (i.e., in addition to passing through filter 230, the Raman signal may pass through additional filter 245, at a 22.5 degree AOI). In one preferred embodiment of the present invention, additional filter 245 is preferably also a long-pass filter. When the Raman signal from the specimen is passed through filter 230, filter 230 serves a second purpose at this time, i.e., it blocks the laser line. Filters 230 and 245 can provide up to >OD10 filtration of the laser line before the light is redirected through focus lens 255 into collecting optical fibers 260. Optical fibers 260 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form.

It should be appreciated that with the constructions shows in FIGS. 1-6, the configurations preferably utilize a 22.5 degree Angle of Optical Incidence (AOI) for filters 25, 30 and/or 45 (or 125, 130 and/or 145, etc.). However, as noted above, any other AOI can also be configured to take advantage of certain manufacturing tolerances.

For example, and looking now at FIG. 7, there is shown another novel Raman probe configuration 305 which uses a different AOI for the filters. With this construction, the output of excitation light source LS is delivered through optical fiber 310 and collimated through lens 315. A bandpass filter 320 (or multiple combination of bandpass filters 320A, 320B) is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 310. Preferably bandpass filter 320 is adapted to block spurious signals associated with both the laser and the fiber. The laser excitation light is then reflected by a filter 325, which in this configuration may be a laser line reflector (at a 40 degree Angle of Optical Incidence, AOI) and a filter 330 (at a 5 degree AOI), and then it is focused through lens 335 to excite specimen 340. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. In one preferred embodiment of the present invention, filter 330 is preferably a long-pass filter. In this embodiment, laser line reflector 325 is preferably a simple reflector to reflect the laser light. After the laser excitation light has been projected on the specimen, the Raman signal is re-collimated through lens 335 and passed through filter 330. Alternatively, the Raman signal may pass through multiple filters (i.e., in addition to passing through filter 330, the Raman signal may pass through additional filter 345, at a 5 degree AOI). In one preferred embodiment of the present invention, additional filter 345 is preferably also a long-pass filter. When the Raman signal from the specimen is passed though filter 330, filter 330 serves a second purpose at this time, i.e., it blocks the laser line. Filters 330 and 345 can provide up to >OD10 filtration of the laser line before the light is redirected through broadband reflector 350 (at a 45 degree AOI) and focus lens 355 into collecting optical fibers 360. Optical fibers 360 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form. In addition to reflecting the Raman signal, broadband reflector 350 also filters out laser excitation light (OD1).

As noted above, Raman probe configuration 305 uses a 5 degree AOI for filters 330 and 345. Such a small AOI can reduce the s and p polarization differences which are associated with a large angle of AOI. By using a smaller AOI value, the Raman signal at around ~300 cm−1 (or smaller) can be readily resolved. In this configuration, laser line reflector (or filter) 325 is designed for a 40 degree AOI. The laser line reflector 325 may be a simple laser line Distributed Bragg Reflector (DBR).

It should be appreciated that with a much narrower bandpass filter and a filter with a much smaller AOI, Raman signals as close as 100 cm−1 can also be readily utilized.

Looking now at FIG. 8, there is shown another novel Raman probe configuration 405 which also uses a smaller AOI for the filters (which are preferably long-pass filters). More particularly, with this construction, the output of excitation light source LS is delivered through optical fiber 410 and collimated through lens 415. A bandpass filter 420 (or multiple combination of bandpass filters 420A, 420B) is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 410. Preferably bandpass filter 420 is adapted to block spurious signals associated with both the laser and the fiber. The laser excitation light is then reflected by a laser line reflector 425 (at a 40 degree Angle of Optical Incidence, AOI) and a filter 430 (at a 5 degree AOI), and then it is focused through lens 435 to excite specimen 440. In this embodiment, laser line reflector 425 is preferably a simple reflector to reflect the laser light. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. In one preferred embodiment of the present invention, filter 430 is preferably a long-pass filter. After the laser excitation light has been projected on the specimen, the Raman signal is re-collimated through lens 435 and passed through filter 430. Alternatively, the Raman signal may pass through multiple filters (i.e., in addition to passing through filter 430, the Raman signal may pass through additional filter 445, at a 5 degree AOI). In one preferred embodiment of the present invention, additional filter 445 is preferably also a long-pass filter. When the Raman signal from the specimen is passed a through filter 430, filter 430 serves a second purpose at this time, i.e., it blocks the laser line. Filters 430 and 445 can provide up to >OD10 filtration of the laser line before the light is redirected by focus lens 455 into collecting optical fibers 460. Optical fibers 460 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form.

Figure 9:
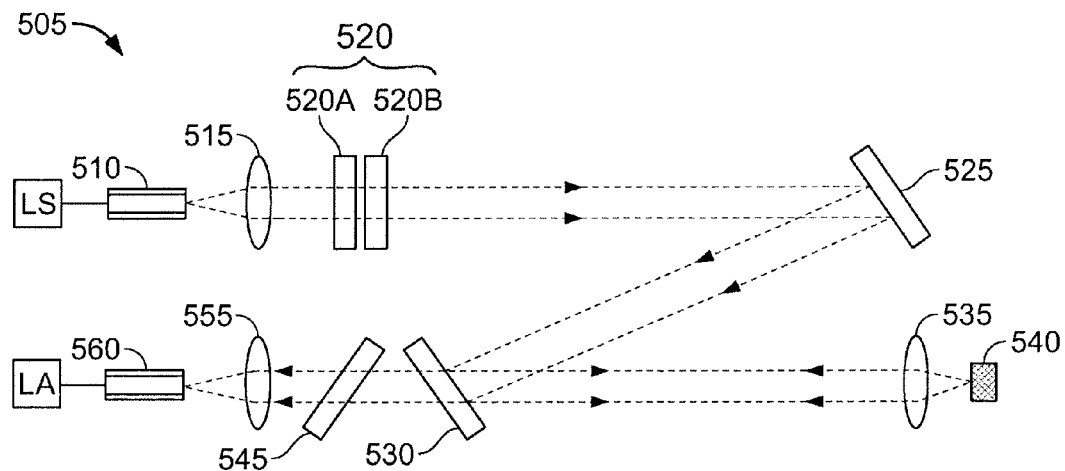
FIG. 9 illustrates another embodiment which is a variation of FIG. 6, except using a 10 degree AOI for the filters.

As noted above, any other angles in the filters can also be used to configure the Raman probe wherein the fibers and signal collecting optics are collinear with one another. Thus, in the construction shown in FIG. 9, the output of excitation light source LS is delivered through optical fiber 510 and collimated through lens 515. A bandpass filter 520 (or multiple combination of bandpass filters 520A, 520B) is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 510. Preferably bandpass filter 520 is adapted to block spurious signals associated with both the laser and the fiber. The laser excitation light is then reflected by filters 525 (at a 10 degree AOI) and 530 (at a 10 degree AOI), and then it is focused through lens 535 to excite specimen 540. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. In one preferred embodiment of the present invention, filters 525 and 530 are preferably long-pass filters. In this respect it should also be appreciated that filter 525 may be replaced by a simple reflector to reflect the laser light. After the laser excitation light has been projected on the specimen, the Raman signal is re-collimated through lens 535 and passed through filter 530. Alternatively, the Raman signal may pass through multiple filters (i.e., in addition to passing through filter 530, the Raman signal may pass through additional filter 545, at a 10 degree AOI). In one preferred embodiment of the present invention, additional filter 545 is preferably also a long-pass filter. When the Raman signal from the specimen is passed through filter 530, filter 530 serves a second purpose at this time, i.e., it blocks the laser line. Filters 530 and 545 can provide up to >OD10 filtration of the laser line before the light is redirected by focus lens 555 into collecting optical fibers 560. Optical fibers 560 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form.

Figure 10:
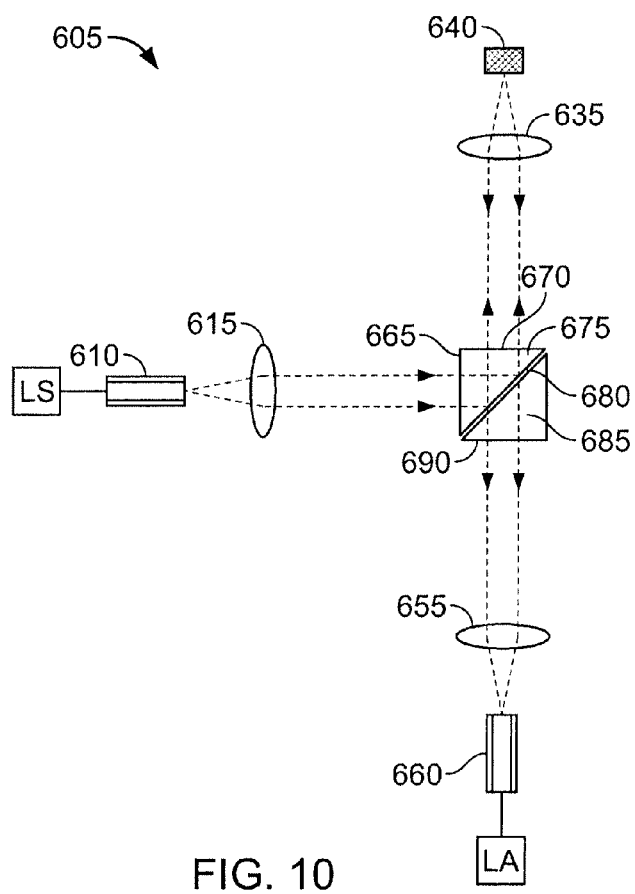
FIG. 10 illustrates another embodiment of Raman probe which is designed to be more compact through the use of two prisms with various coatings on the surface.
Figure 13:
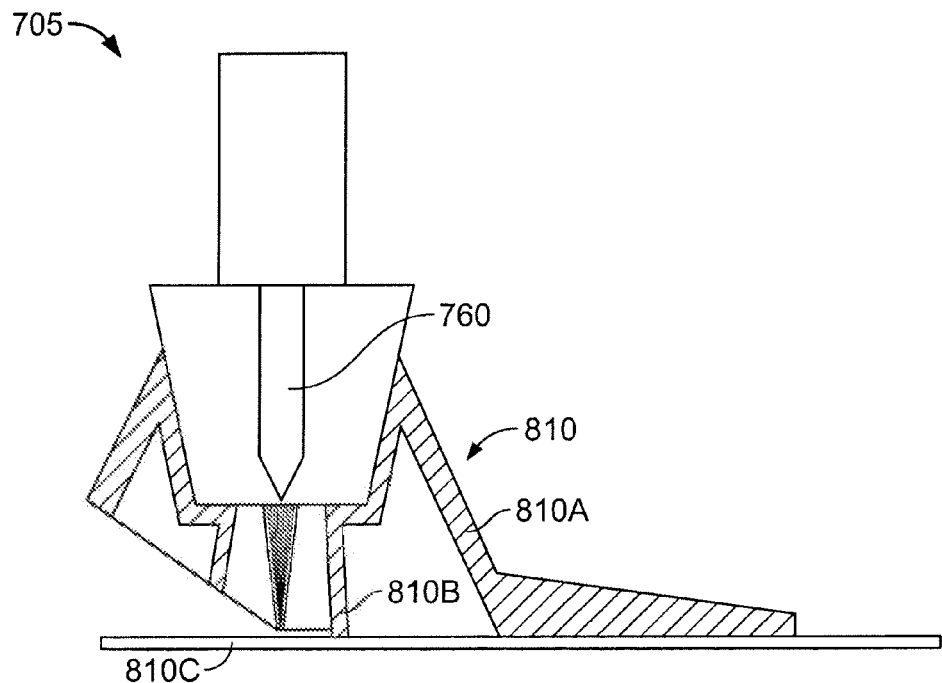

The Raman probe can also be made significantly more compact by utilizing two prisms with various coatings on their surfaces. One such embodiment is illustrated in FIG. 10. In this configuration, the functions of the various coatings are the same as discussed above. More particularly, in FIG. 10 there is shown a Raman probe configuration 605. The output of excitation light source LS is delivered through optical fiber 610 and collimated through lens 615. A bandpass filter coating 665 on a first prism 675 is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 610. Preferably bandpass filter 620 is adapted to block spurious signals associated with both the laser and the fiber. The laser excitation light is then reflected by a dichroic beamsplitter coating 680, at a 45 degree AOI, through a broadband AntiReflection (AR) coating 670 and then it is focused through lens 635 to excite specimen 640. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. After the laser excitation light has been projected on the specimen, the Raman signal is re-collimated through lens 635 and passed through broadband AR coating 670. When the Raman signal from the specimen is passed though broadband AR coating 670, broadband AR coating 670 serves a second purpose at this time, i.e., it blocks the laser line. The light passes through second prism 685, and then through filter coating 690 before being redirected by focus lens 655 into collecting optical fibers 660. Optical fibers 660 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form.

Portable Raman Probe with Inline Vial Capability

Raman optical probes of the type shown in FIGS. 1-10 may be used for delivery and collection of light to and from the specimen in a variety of settings. However, usability challenges can arise when trying to utilize such a Raman optical probe in portable field applications.

By way of example, with the construction shown in FIG. 1, the distance from delivery/collection lens 35 and the specimen 40 must generally be kept to within approximately +/−0.5 mm of the focal length of lens 35 so as to maximize the signal strength.

In addition, many users may desire to maintain the specimen 40 close to the lens 35, while not actually touching the specimen, so as to avoid contaminating the Raman probe instrument with the specimen.

Also, some users may prefer to have their specimens placed in a glass vial during measurement. This can be awkward with prior art Raman probes.

To address these and other concerns, the present invention provides a novel Raman probe which may be used in three different modes of use. In a first mode of use, the Raman probe allows the user to maintain a distance from the specimen using a conical standoff, which provides both distance control and laser safety by limiting the exposed beams. The second mode of use allows the user to remove the conical standoff so as to maintain distance control by hand or other means. The third mode of use allows a specimen vial to be inserted directly within the probe optics assembly.

More particularly, and looking now at FIG. 11, there is shown a novel Raman probe configuration 705 which provides the three aforementioned modes of use. With this construction, the output of excitation light source LS is delivered through optical fiber 710 and collimated through lens 715. A bandpass filter 720 (or multiple combination of bandpass filters 720A, 720B) is used to pass the laser excitation light and to block spurious signals associated with the laser, the fiber, and/or both. The spurious signals associated with the laser generally comprise ASE from the laser, and the spurious signals associated with the fiber generally comprise fluorescence and Raleigh and Raman scatterings generated inside the fiber 710. Preferably bandpass filter 720 is adapted to block spurious signals associated with both the laser and the fiber. The laser excitation light is then reflected by a laser line reflector 725 (e.g., at a 22.5 degree Angle of Optical Incidence, AOI) and a filter 730 (e.g., at a 22.5 degree AOI), and then it is focused through lens 735 on specimen vial receptacle 805, or passed through the specimen vial receptacle 805 and through a focus lens 800, and then through another focus lens 795, to a specimen location 740. In this respect it should be appreciated that, for the purposes of the present disclosure, certain AOI values are used, however, in accordance with the present invention, the AOI may vary from one embodiment to another. Moreover, since the geometry of the input fiber and output fiber does not need to be parallel or perpendicular, AOI values may vary with the particular geometry employed, e.g., the AOI values may be anywhere from 5 degree AOI to 50 degree AOI. In one preferred embodiment of the present invention, filter 730 is preferably a long-pass filter. In this embodiment, laser line reflector 725 is preferably a simple reflector to reflect the laser light. After the laser excitation light has been projected on the specimen, the Raman signal is re-collimated through lens 735 (where the specimen is located in vial receptacle 805), or lenses 795, 800 and 735 (where the specimen is located at specimen location 740) and passed through filter 730. Alternatively, the Raman signal may pass through multiple filters (i.e., in addition to passing through filter 730, the Raman signal may pass through additional filter 745 (e.g., at a 22.5 degree AOI). In one preferred embodiment of the present invention, additional filter 45 is preferably also a long-pass filter. When the Raman signal from the specimen is passed through filter 730, filter 730 serves a second purpose at this time, i.e., it blocks the laser line. Filters 730 and 745 can provide up to >OD10 filtration of the laser line before the light is redirected by focus lens 755 into collecting optical fibers 760. Optical fibers 760 transmit the Raman signal to a light analyzer LA which analyzes the Raman signature of the specimen, whereby to identify the specimen. The light analyzer LA may comprise a spectrometer with associated analysis apparatus of the sort well known in the art. See, for example, FIG. 1A, which shows the overall Raman spectroscopy system in schematic form. In one preferred embodiment of the invention, filters 730 and/or 745 may comprise long-pass filters.

The novel Raman probe 705 may be implemented and used as follows.

Looking first at FIGS. 12, 13, 14 and 14A, in the first mode of use, the novel Raman probe 705 allows the user to maintain distance to the specimen using a conical standoff 810 which mounts to the housing 815 of the Raman probe adjacent to output fiber 760. The conical standoff 810 is designed to provide both distance control and laser safety (by limiting beam exposure). Conical standoff 810 can be manufactured as a disposable element so as to alleviate contamination concerns, or it can be a more permanent element of the Raman probe. In one preferred construction, the probe and conical standoff include a mechanism for attaching and removing a permanent or disposable conical standoff to and from a portable Raman unit. Among other things, the conical standoff may be snap fit to the remainder of the probe (see FIG. 14), or the conical standoff may be pivotally attached to the remainder of the probe so that it may be swung into and out of position as desired.

The conical standoff 810 may comprise a variety of configurations, e.g., such as those shown in FIGS. 12-14 and 14A. In one preferred form of the invention, conical standoff 810 comprises an outer cone 810A (FIG. 13) which serves as the distance standoff and an inner cone 810B which provides eye safety. Preferably, the inner cone 810B is backpainted to conceal laser light. The conical standoff can be made from plastic or metal or a combination of the two materials. A glass window 810C (FIG. 12) may be provided at the point of laser emission to prevent the specimen from penetrating into the cone. Optionally, a switch (not shown) in conical standoff 810 may be provided to trigger laser emission on contact with the sample. If desired, conical standoff 810 may comprise a half-moon filter 810D (FIG. 14A) surrounding the outer perimeter of outer cone 810A, where the filter elements 810E are configured to filter out the operative wavelength of the laser so as to prevent direct viewing of the laser beam and thereby provide operator safety.

The second mode of use allows the user to remove the conical standoff 810 so as to maintain the desired distance manually or with other means. This mode also allows the user to avoid having to touch the specimen which, again, can help alleviate contamination concerns. In this second mode, it is also possible to couple the use of an electronic/optical method to provide a feedback signal which is proportional to the distance between the specimen and the lens in order to optimize the Raman signal.

Figure 15:
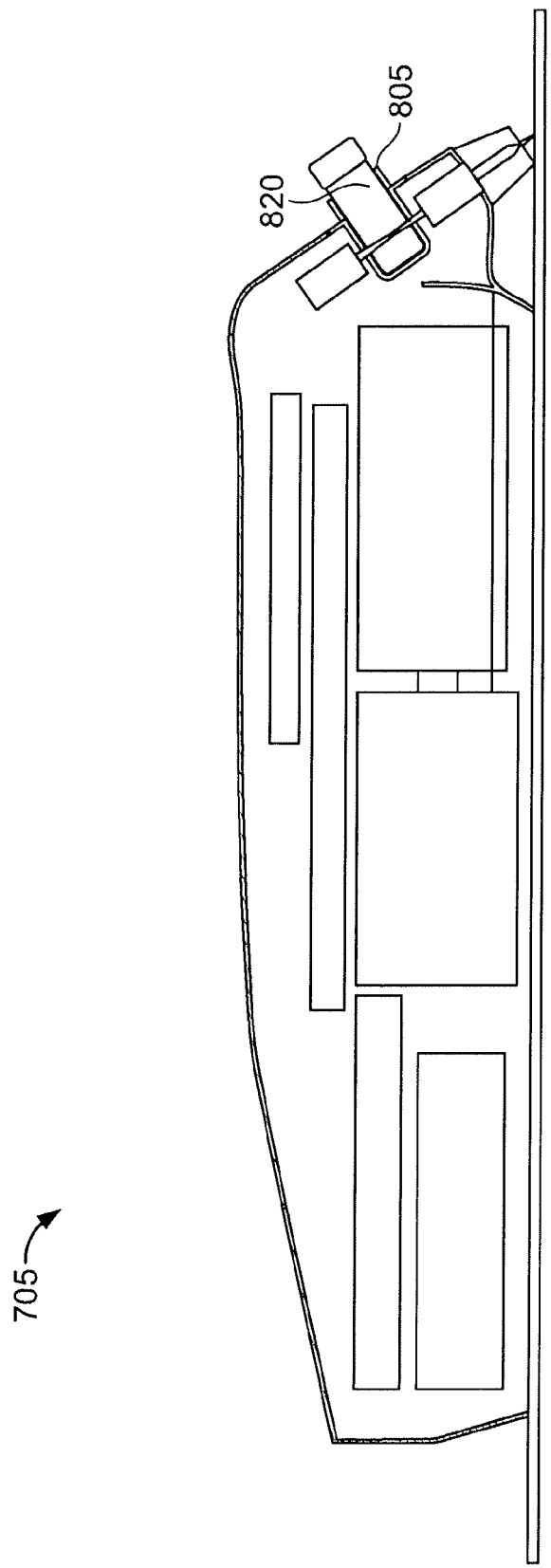
FIGS. 15-17 illustrate the portable Raman probe of FIG. 11 configured to allow the user to insert a specimen vial directly within the probe optics assembly.
Figure 16:
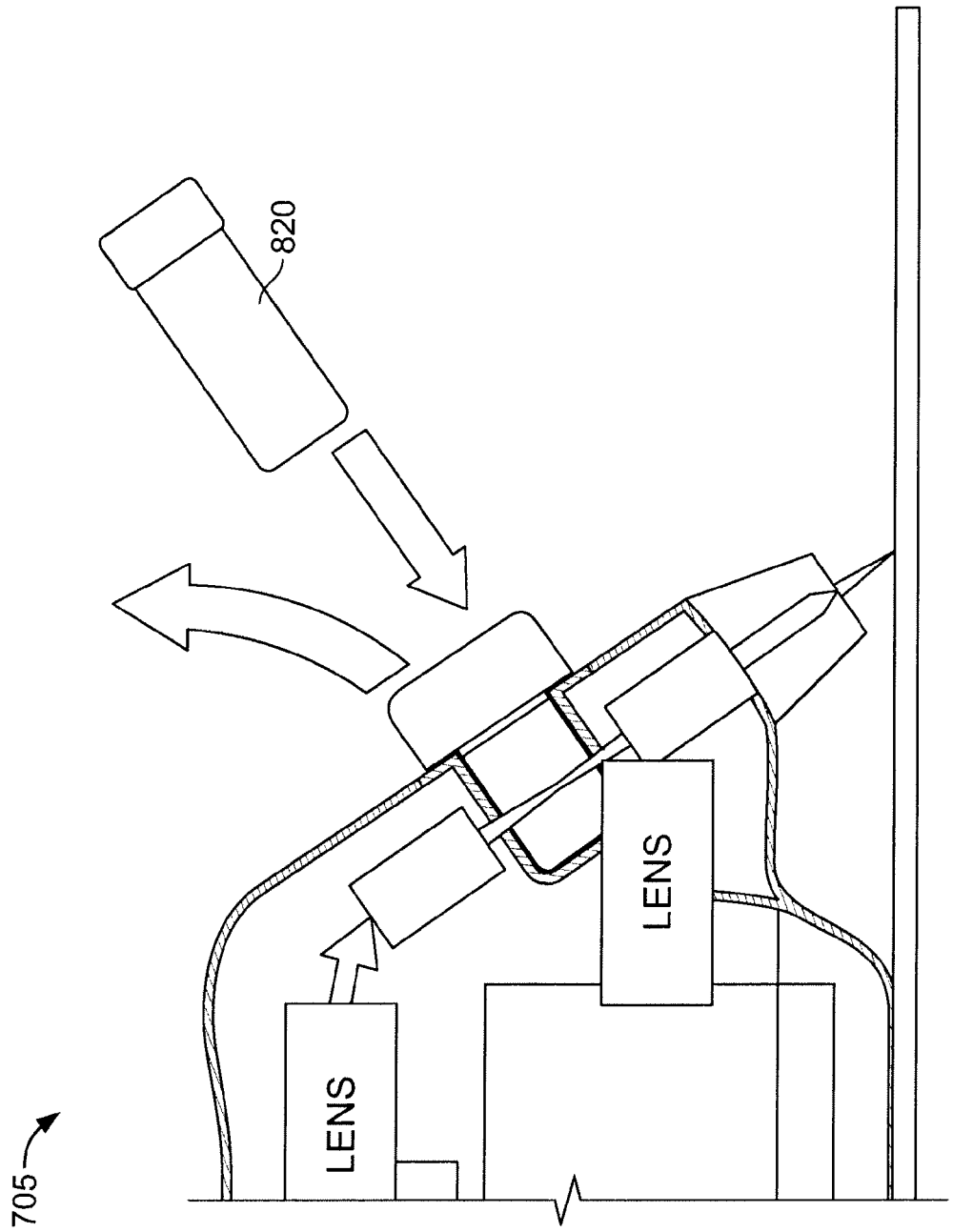
Figure 17:
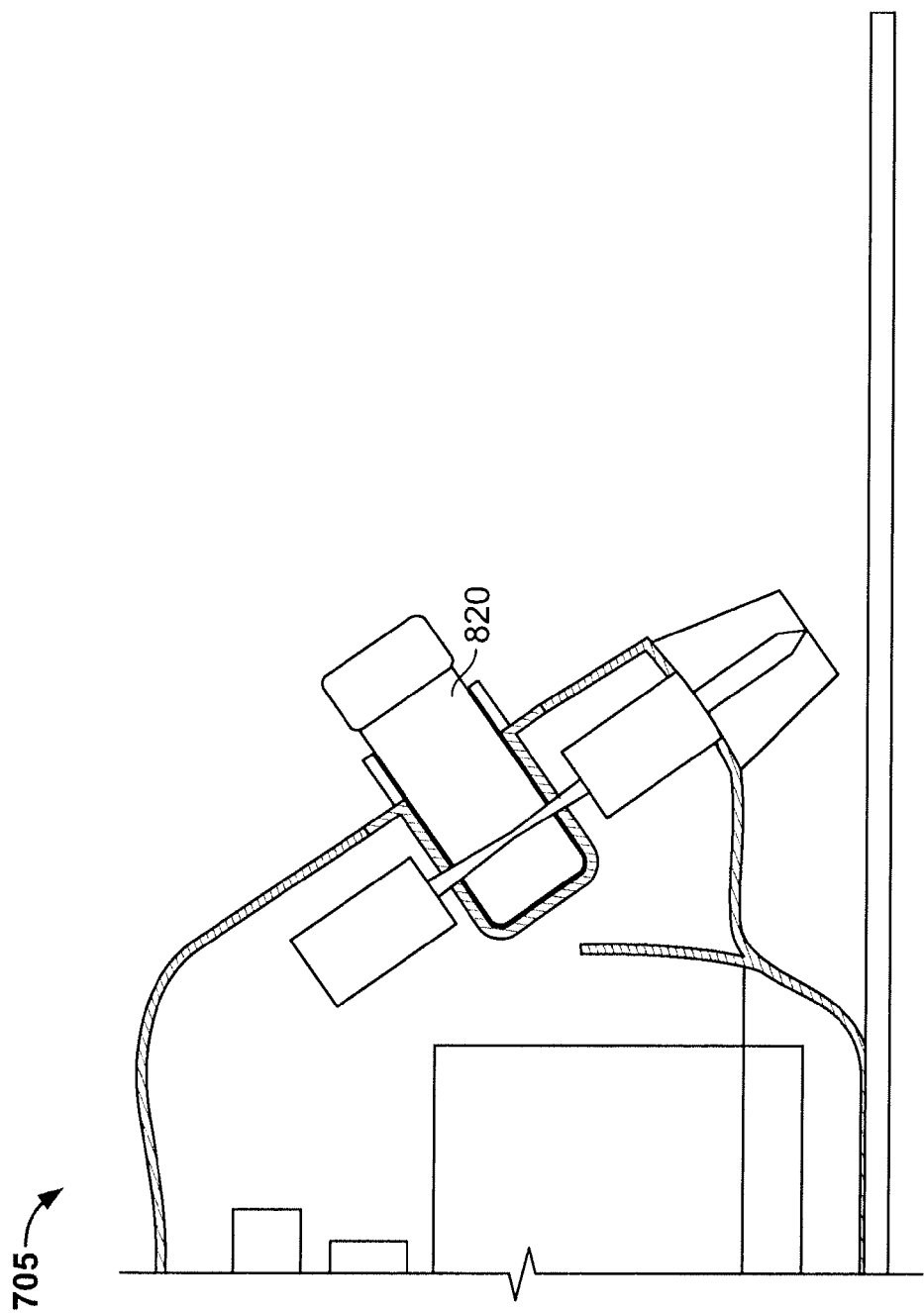
Figure 18:
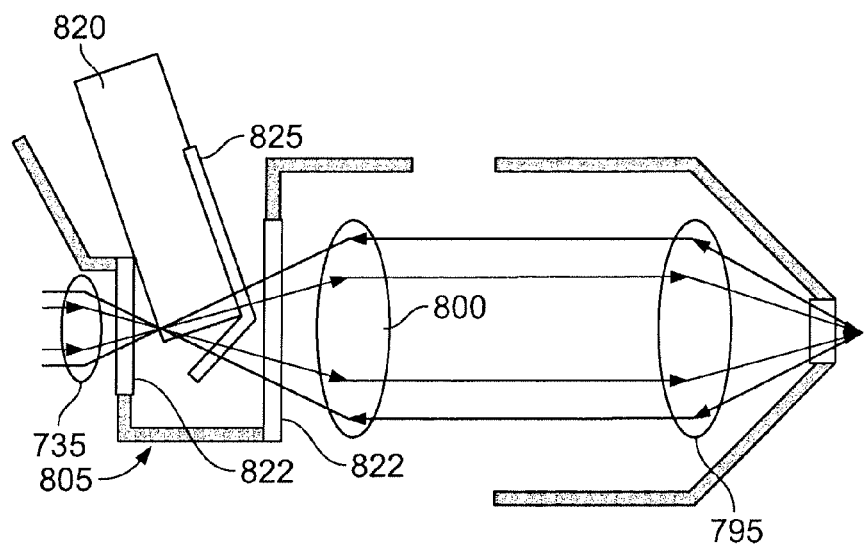
FIG. 18 is a schematic view showing a specimen vial inserted directly within the probe optics assembly, wherein the specimen vial incorporates a shutter to prevent stray backlight from entering the vial receptacle.

In the third mode of use, and looking now at FIGS. 15-17, a vial 820 may be inserted in vial receptacle 805 so that the vial 820 sits within the probe optics assembly. The additional optics permit the light to be focused on a vial 820 in the receptacle 805 (if one is present) or deliver the light to a standoff specimen at 740 (if the vial is not present). The receptacle 805 preferably incorporates a water tight barrier between the interior of the receptacle and the working elements of the probe. Windows 822 (FIG. 18) permit light to pass into and out of receptacle 805.

If desired, vial 820 can include a "shutter" 825 to close off the window 822 adjacent to lens 800 so as to prevent stray backlight from entering receptacle 805 when the specimen is retained in receptacle 805.

Figure 14:
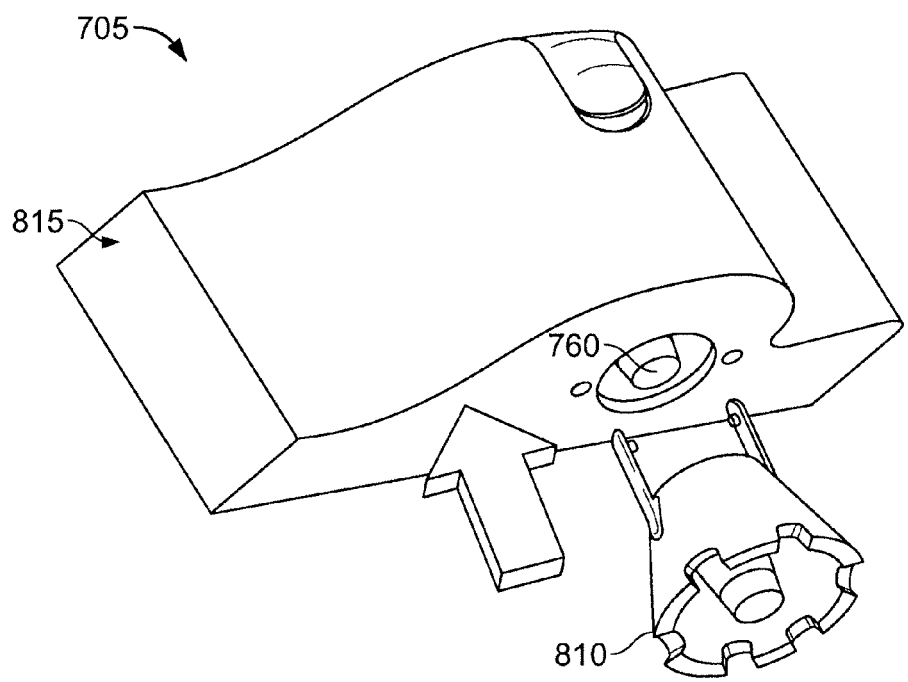
FIG. 14 illustrates the portable Raman probe of FIG. 11 configured to allow the user to remove the conical standoff so as to maintain distance control by hand or other means.
Figure 14A:
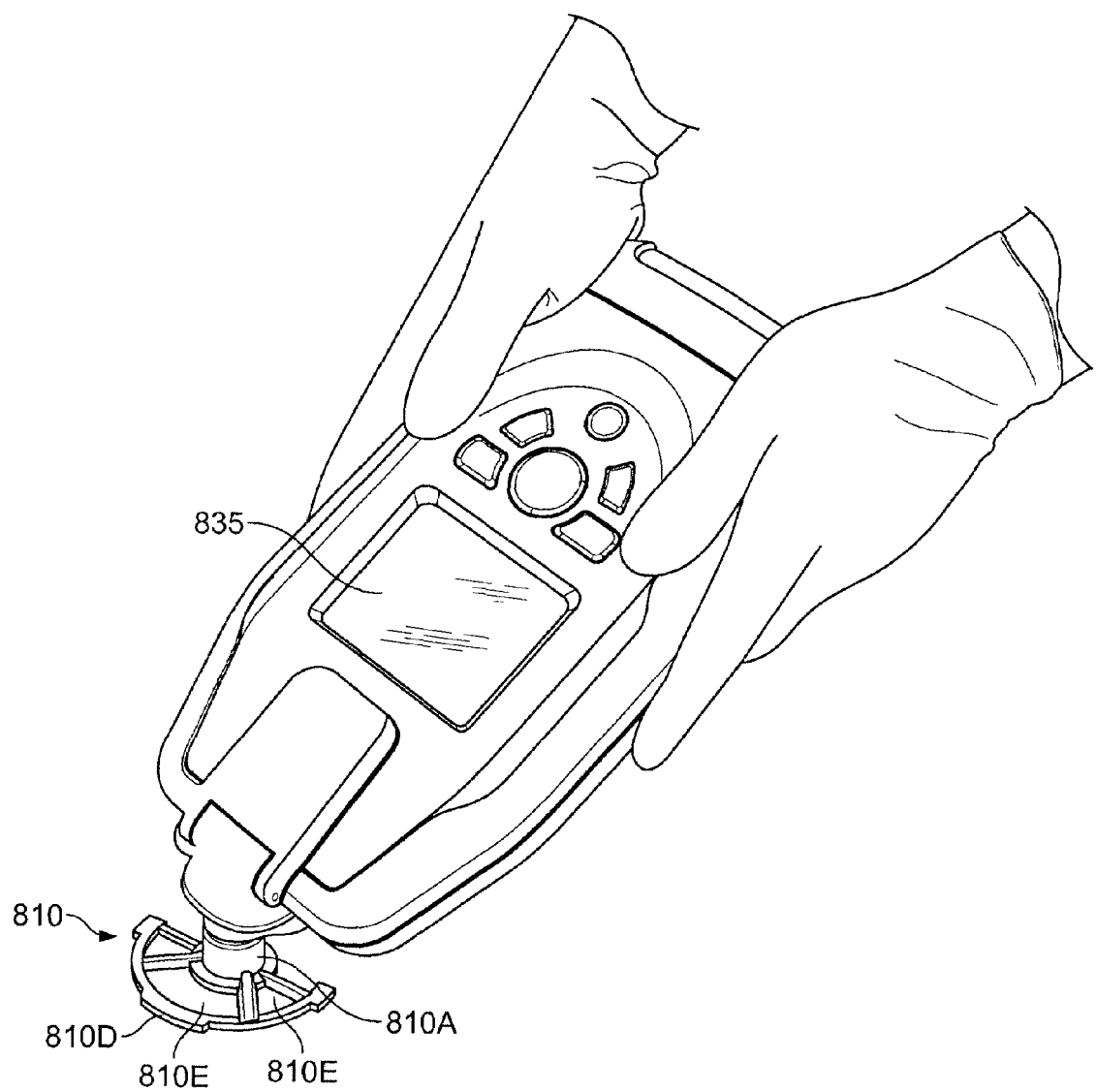
FIG. 14A illustrates a novel portable Raman probe with another form of conical standoff.
Figure 19:
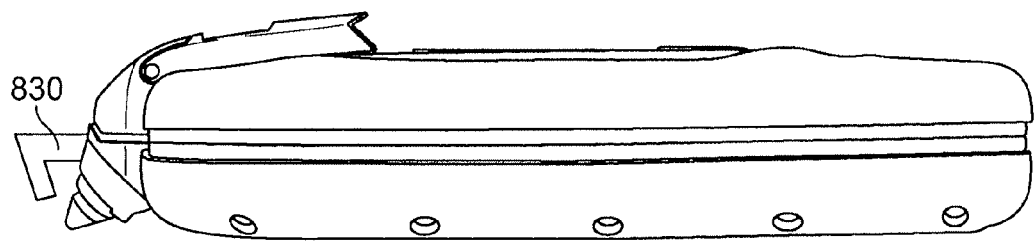
FIG. 19 is a schematic view showing a camera mounted to the front of the Raman probe.

Looking next at FIG. 19, a camera 830 may be added to the front of the probe, with the image from the camera being displayed on the probe's screen 835 (FIG. 14A). With this construction, the operator can position the probe relative to a specimen at a standoff location 740 while looking at screen 835. This feature can enhance eye safety and, additionally, by providing camera magnification, can assist in positioning the Raman pump beam at the correct location. Furthermore, the data from camera 830 can be stored, along with date and time information, etc., in a removable memory chip (e.g., a CompactFlash card) so as to permit easy documentation of a probe test.

Further Constructions

It is to be understood that the present invention is by no means limited to the particular constructions herein disclosed and/or shown in the drawings, but also comprises any modifications or equivalents within the scope of the invention.

What is claimed is:

1. A Raman probe comprising:
a first optical fiber for receiving laser excitation light from a light source and transmitting the same;
a first spectral filter for receiving light from the first optical fiber and adapted to pass the laser excitation light and to block spurious signals associated with the light;
a second spectral filter for receiving light from the first spectral filter and adapted to direct the light toward a specimen;
focusing apparatus for receiving the light from the second spectral filter, focusing the light on the specimen so as to generate the Raman signal, and returning the Raman signal to the second spectral filter, wherein the second spectral filter is further configured so that when the second spectral filter receives the Raman signal from the focusing apparatus, the second spectral filter filters out laser excitation light before directing the Raman signal to a broadband reflector; and
a broadband reflector disposed between the second spectral filter and a second optical fiber,
wherein the broadband reflector is configured to receive the Raman signal from the second spectral filter, to reflect the Raman signal to the second optical fiber, and to transmit laser excitation light; and
wherein the second optical fiber receives the Raman signal from the broadband reflector and transmits the same to a light analyzer.

2. A Raman probe according to claim 1 further comprising a light source.

3. A Raman probe according to claim 2 wherein the light source comprises at least one 785 nm semiconductor laser with limited linewidth.

4. A Raman probe according to claim 3 wherein the light source has a linewidth <0.2 nm FWHM.

5. A Raman probe according to claim 1 further comprising a lens disposed between the first fiber and the first filter for collimating light from the first fiber on the first filter.

6. A Raman probe according to claim 1 wherein the spurious signals associated with the light comprise spurious signals associated with a laser that produces the laser excitation light, the fiber, and/or both.

7. A Raman probe according to claim 6 wherein the spurious signals associated with the laser comprise amplified spontaneous emission.

8. A Raman probe according to claim 1 wherein the spurious signals associated with the light comprise spurious signals associated with the fiber.

9. A Raman probe according to claim 8 wherein spurious signals associated with the fiber comprise fluorescence.

10. A Raman probe according to claim 8 wherein the spurious signals associated with the fiber comprise Rayleigh and Raman scatterings.

11. A Raman probe according to claim 1 wherein the spurious signals associated with the light comprise spurious signals associated with both a laser that produces the laser excitation light and the fiber.

12. A Raman probe according to claim 1 wherein the first filter is adapted to block amplified spontaneous emission from a laser that produces the laser excitation light and fluorescence and Rayleigh and Raman scatterings generated inside the first fiber.

13. A Raman probe according to claim 1 wherein the first filter comprises a bandpass filter.

14. A Raman probe according to claim 13 wherein the bandpass filter comprises a plurality of bandpass filter units working in combination with one another.

15. A Raman probe according to claim 1 wherein the first filter is adapted to filter out amplified spontaneous emission background in the Raman domain of >300 $cm^{-1}$.

16. A Raman probe according to claim 1 wherein the second filter comprises a plurality of filter units working in combination with one another.

17. A Raman probe according to claim 16 wherein the second filter comprises three or more filter units working in combination with one another.

18. A Raman probe according to claim 1 wherein the second filter comprises a filter unit working in combination with a reflector unit.

19. A Raman probe according to claim 1 wherein a normal to a surface of the second filter is oriented at an angle of 22.5 degrees with respect to an optical path of the Raman signal between the specimen and the second filter.

20. A Raman probe according to claim 1 wherein a normal to a surface of the second filter is oriented at an angle of 5 degrees with respect to an optical path of the Raman signal between the specimen and the second filter.

21. A Raman probe according to claim 1 wherein a normal to a surface of the second filter is oriented at an angle of 10 degrees with respect to an optical path of the Raman signal between the specimen and the second filter.

22. A Raman probe according to claim 1 wherein the second filter comprises a long-pass filter.

23. A Raman probe according to claim 22 wherein the long-pass filter is adapted to filter out the amplified spontaneous emission background in the Raman domain of >300 $cm^{-1}$.

24. A Raman probe according to claim 22 wherein the long-pass filter comprises a plurality of long-pass filter units working in combination with one another.

25. A Raman probe according to claim 24 wherein the long-pass filter comprises three or more long-pass filter units working in combination with one another.

26. A Raman probe according to claim 22 wherein the long-pass filter comprises a long-pass filter unit working in combination with a reflector unit.

27. A Raman probe according to claim 1 wherein the focusing apparatus comprises a lens disposed between the second filter and the specimen.

28. A Raman probe according to claim 1 wherein the focusing apparatus comprises a first lens for receiving light from the second filter, a vial receptacle for receiving light from the first lens, a second lens for receiving light from the vial receptacle, a third lens for receiving light from the second lens and focusing that light on a target location, and wherein the focusing apparatus is adapted so that: (i) when the specimen is located in the vial receptacle, light is focused on the specimen; and (ii) when the specimen is not located in the vial receptacle, light is focused at the target location.

29. A Raman probe according to claim 28 wherein the first lens, vial receptacle, second lens, third lens and target location are all aligned with one another.

30. A Raman probe according to claim 1 wherein the second filter is adapted to provide up to OD10 filtration of the laser excitation light before reflecting the Raman signal to a second optical fiber.

31. A Raman probe according to claim 1 wherein the broadband reflector is adapted to provide filtering of the laser excitation light of OD1 or more before reflecting the Raman signal to the second optical fiber.

32. A Raman probe according to claim 1 wherein the broadband reflector reflects Raman signal of>300 $cm^{-1}$, and passes Raman signal of 0 to 300 $cm^{-1}$.

33. A Raman probe according to claim 1 wherein a normal to a surface of the broadband reflector is oriented at an angle of 45 degrees with respect to an optical path of the Raman signal between the specimen and the second filter.

34. A Raman probe according to claim 1 further comprising a lens disposed between the second filter and the second fiber.

35. A Raman probe according to claim 1 further comprising a light analyzer.

36. A Raman probe according to claim 35 wherein the light analyzer comprises a spectrometer.

37. A Raman probe according to claim 35 wherein the light analyzer comprises a spectrometer and associated analysis apparatus configured to analyze the Raman signal and to identify the specimen based on the Raman signal.

38. A method for conducting Raman spectroscopy of a specimen, comprising:
generating laser excitation light using a light source;
passing the laser excitation light through a first spectral filter so as to block spurious signals associated with the light;
directing the laser excitation light to a second spectral filter so as to direct the laser excitation light toward the specimen;
receiving the light from the second spectral filter, focusing the light on the specimen so as to generate the Raman signal, and returning the Raman signal to the second spectral filter, wherein the second spectral filter is further configured so that when the second spectral filter receives the Raman signal from the specimen, the second spectral filter filters out unwanted laser excitation light;
passing the filtered light received from the second spectral filter to a broadband reflector configured to reflect the Raman signal to a light analyzer and to transmit laser excitation light; and
analyzing the Raman signal from the specimen to identify the specimen.

39. The method of claim 38, wherein the broadband reflector filters laser excitation light from the light received from the second filter.

40. The method of claim 39, wherein the broadband reflector provides filtering of laser excitation light of OD1 or more from the light received from the second filter.

41. The method of claim 38, wherein the broadband reflector reflects Raman signal of 300 $cm^{-1}$ or more, and transmits Raman signal of between 0 $cm^{-1}$ and 300 $cm^{-1}$.

42. A Raman probe comprising:
a first optical fiber for receiving laser excitation light from a light source and transmitting the same;
a first filter for receiving light from the first optical fiber and adapted to pass the laser excitation light and to block spurious signals associated with the light;
a second filter for receiving laser excitation light from the first filter and adapted to direct the light toward a specimen;
focusing apparatus for receiving the laser excitation light from the second filter, focusing the light on the specimen so as to generate the Raman signal, and returning the Raman signal to the second filter, wherein the second filter is further configured so that when the second filter receives the Raman signal from the focusing apparatus, the second filter filters out laser excitation light before directing the Raman signal to a second optical fiber; and
a second optical fiber for receiving the Raman signal from the second filter and transmitting the same to a light analyzer,
wherein the focusing apparatus comprises a first lens for receiving laser excitation light from the second filter, a vial receptacle for receiving light from the first lens, a second lens for receiving light from the vial receptacle, a third lens for receiving light from the second lens and focusing that light on a target location, and wherein the focusing apparatus is adapted so that: (i) when the specimen is located in the vial receptacle, light is focused on the specimen; and (ii) when the specimen is not located in the vial receptacle, light is focused at the target location.

43. The Raman probe of claim 42, wherein the first lens, the vial receptacle, the second lens, the third lens, and the target location are aligned along a common optical path.

44. The Raman probe according to claim 1, wherein each of the first and second spectral filters comprises multiple layers of dielectric material.

45. The method of claim 38, wherein each of the first and second spectral filters comprises multiple layers of dielectric material.

* * * * *